United States Patent
Ciammaichella et al.

(10) Patent No.: US 6,436,508 B1
(45) Date of Patent: Aug. 20, 2002

(54) ABSORBENT ARTICLES HAVING A LIQUID SWELLABLE MATERIAL COATED BREATHABLE BACKSHEET

(75) Inventors: Fabio Ciammaichella, Pescara (IT); Michael Divo, Friedrichsdorf (DE); Italo Corzani, Chieti (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/463,105

(22) PCT Filed: Jul. 23, 1998

(86) PCT No.: PCT/US98/15283

§ 371 (c)(1),
(2), (4) Date: Apr. 19, 2000

(87) PCT Pub. No.: WO99/04739

PCT Pub. Date: Feb. 4, 1999

(30) Foreign Application Priority Data

Jul. 25, 1997 (BE) ............................................. 97112813

(51) Int. Cl.[7] ................................................. B32B 3/10
(52) U.S. Cl. ....................... 428/131; 428/221; 428/340; 428/137; 428/368; 428/375
(58) Field of Search ................................. 428/131, 221, 428/340, 137, 368, 375

(56) References Cited

U.S. PATENT DOCUMENTS

| | | |
|---|---|---|
| 3,156,242 A | 11/1964 | Crowe, Jr. |
| 3,426,754 A | 2/1969 | Bierenbaum et al. |
| 3,881,489 A | 5/1975 | Hartwell |
| 3,989,867 A | 11/1976 | Sisson |
| 4,235,237 A | 11/1980 | Mesek et al. |
| 4,341,216 A | 7/1982 | Obenour |
| 4,591,523 A | 5/1986 | Thompson |
| 4,592,751 A | 6/1986 | Gegelys |
| 4,636,207 A | 1/1987 | Buell |
| 4,648,876 A | 3/1987 | Becker et al. |
| 4,681,578 A | 7/1987 | Anderson et al. |
| 4,681,793 A | 7/1987 | Linman et al. |
| 4,713,068 A | 12/1987 | Wang et al. |
| 4,828,556 A | 5/1989 | Braun et al. |
| 4,887,602 A | 12/1989 | O'Leary |
| 4,900,317 A | 2/1990 | Buell |
| 5,019,066 A | 5/1991 | Freeland et al. |
| 5,085,654 A | 2/1992 | Buell |
| 5,447,788 A | 9/1995 | Rhim et al. |
| 5,492,751 A | 2/1996 | Butt, Sr. et al. |
| 5,527,302 A | 6/1996 | Endres et al. |
| 5,531,729 A | 7/1996 | Coles et al. |
| 5,549,775 A | 8/1996 | Odorzynski |
| 5,571,096 A | 11/1996 | Dobrin et al. |
| 5,628,737 A | 5/1997 | Dobrin et al. |
| 5,718,698 A | 2/1998 | Dobrin et al. |
| 5,733,628 A | 3/1998 | Pelkie |
| H1750 H | 9/1998 | Dorbin |
| 5,843,056 A | 12/1998 | Good et al. |
| 5,843,057 A | 12/1998 | McCormack |
| 5,843,066 A | 12/1998 | Dobrin |
| 5,865,823 A | 2/1999 | Curro |
| 5,868,725 A | 2/1999 | Coles et al. |
| 5,951,534 A | 9/1999 | Cummings et al. |
| 5,997,521 A | 12/1999 | Robles et al. |

FOREIGN PATENT DOCUMENTS

| | | |
|---|---|---|
| DE | 44 34 171 A1 | 3/1996 |
| EP | 0 140 476 A2 | 5/1985 |
| EP | 0 710 472 A1 | 5/1996 |
| EP | 0 401 189 B2 | 6/1996 |
| EP | 0 780 108 A1 | 6/1997 |
| GB | 2 203 985 A | 11/1988 |
| WO | WO 91/00077 | 1/1991 |
| WO | WO 97/15258 | 5/1997 |

*Primary Examiner*—Blaine Copenheaver
*Assistant Examiner*—Hai Vo
(74) *Attorney, Agent, or Firm*—Ingrid N. Hickman; Jeffrey V. Bamber

(57) ABSTRACT

The present invention relates to absorbent article such as sanitary napkins and panty liners comprising a topsheet, absorbent core, and backsheet which are breathable by the incorporation of a breathable backsheet and have a reduced tendency to exhibit garment wet through. The backsheet comprises at least one air permeable layer such as an apertured formed film or fibrous layer which is applied and preferably coated with a non-soluble, liquid swellabe material, such as polyvinyl alcohol. Upon contact with fluid discharge, the material swells and closes the apertures of the layer, thereby reducing air permeability and preventing the passage of liquid through the layer and thus through the backsheet onto the garment of the wearer of the article.

3 Claims, No Drawings

ABSORBENT ARTICLES HAVING A LIQUID SWELLABLE MATERIAL COATED BREATHABLE BACKSHEET

FIELD OF THE INVENTION

The present invention relates to the provision of breathable backsheets for use in absorbent articles which are activated when contacted with liquids to prevent garment wet through.

BACKGROUND OF THE INVENTION

The primary consumer needs which underlie development in the absorbent article field, in particular catamenials is the provision of products providing both a high protection and comfort level.

One means for providing consumer comfort benefits in absorbent articles is by the provision of breathable products. Breathability has typically concentrated on the incorporation of so called 'breathable backsheets' in the absorbent articles. Commonly utilised breathable backsheets are microporous films and apertured formed films having directional fluid transfer as disclosed in for example U.S. Pat. No. 4,591,523. Both these types of breathable backsheets are vapour permeable allowing gaseous exchange with the environment. This thereby allows for the evaporation of a portion of the fluid stored in the core and increases the circulation of air within the absorbent article. The latter is particularly beneficial as it reduces the sticky feeling experienced by many wearers during use, commonly associated with the presence of an apertured formed film or film like topsheet, particularly over extended periods of time. This is a result of topsheets designed to achieve a clean and dry appearance. These topsheets tend to be smooth thereby minimising the build up of fluid on the surface of the topsheet. However, these benefits are achieved at the expense of comfort, particularly under hot and humid conditions, when due to their smooth surface texture they tend to become sticky to the skin.

However, the main drawback associated with the use of breathable backsheets in absorbent articles is the negative effect on the protection level performance, by leakage known as wet through onto the users garment. Although, breathable backsheets in principle only allow the transfer of materials in the gaseous state, physical mechanisms such as extrusion, diffusion and capillary action may still occur and result in the transfer of the fluids from the absorbent core through the backsheet and onto the users garments. In particular, these mechanisms become more dominant if the product is utilised during physical exertion, or for heavy discharge loads or over extended periods of time. Thus, whilst the incorporation of breathable backsheets in absorbent articles is highly desirable from a comfort standpoint, since the primary role of a backsheet still remains the prevention of liquid leakage, such breathable backsheets cannot be satisfactorily incorporated into products.

The problem of wet through onto users garments due to the incorporation of such breathable backsheets in absorbent articles has indeed also been recognised in the art. Attempts to solve the problem have mainly resided in the use of multiple layer backsheets such as those illustrated in U.S. Pat. No. 4,341,216. Similarly EPO 710 471 discloses a breathable backsheet comprising an outer layer of a gas permeable, hydrophobic, polymeric fibrous fabric and an inner layer comprising an apertured formed film having directional fluid transport. The backsheet construction preferably has no liquid transport or wet through under certain specified test conditions. Also EPO 710 472 discloses a breathable backsheet consisting of at least two breathable layers which are unattached to one another over the core area. The backsheet construction preferably has no liquid transport or wet through under certain specified test conditions.

U.S. Pat. No. 4,713,068 discloses a breathable clothlike barrier for use as an outer cover for absorbent articles. The barrier comprises at least 2 layers, a first layer having a specified basis weight, fibre diameter and pore size and a second layer comprising a continuous film of polyvinyl alcohol having a specified thickness. The barrier also has a specified water vapour transmission rate and level of impermeability.

However, none of the above proposed solutions have been able to provide a fully satisfactory solution to the problem of breathable backsheet wet through under all conditions. Furthermore, another problem associated with the exemplified multi layer backsheets is an increase in total thickness of the product and a reduction in the flexibility, both of which result in a consumer noticeable reduction in product comfort.

An alternative proposed solution to the problem of breathable backsheet wet through relates to the improvement of the absorbent material such that little or no liquid comes into contact with the backsheet, thereby preventing wet through. This is typically achieved by increasing the amount of absorbent material in the article. However, this results in an absorbent article which is extremely thick which is highly undesirable from a consumer comfort standpoint. Hence, the absorbent article whilst having the required protection level and still maintaining some comfort benefits by the presence of the breathable backsheet, suffers from a lack of comfort from a different source, in this case the increased dimensions of the article.

In addition the above solution also results in a reduction in the flexibility of the article, particularly evident as an increase in the cross section stiffness. It is however also well established that in order to be comfortable for the wearer absorbent articles need to be cross sectionally flexible. It is believed that the more cross sectionally flexible an absorbent article is, the less will it be noticeable to the wearer. Thus flexibility is another highly desirable comfort requirement of modem absorbent articles.

EPO 705 583 and EPO 705 584 propose longitudinally flexible absorbent articles which are vapour permeable. However, the exemplified absorbent articles are typically very thin and do not address the absorbency capacity of the article or the problem of wet through.

U.S. Pat. No. 5,447,788 discloses a porous nonwoven liquid activated barrier suitable for use in absorbent articles. The barrier includes a fibrous nonwoven web in which at least 50% of the fibres are prepared from a liquid swellable polymer which is not significantly soluble in water such as swellable polyvinyl alcohols. In the presence of water the polymers swell to an extent sufficient to substantially block the passage of liquid through the fibrous nonwoven web. However, from the data given in the patent, the passage of liquids is not substantially blocked and thus these webs do not eliminate the wet through problem.

Consequently, as the incorporation of breathable backsheets in absorbent articles results in reduction of the protection level, further desirable product comfort modifications such as reducing the thickness of the product and improving the flexibility of the product which would further acerbate the problem, may not be incorporated in the absorbent article. Thus, there exists a dichotomy in the means available to provide increased consumer comfort in absorbent products and acceptable protection levels.

It is therefore an objective of the present invention to provide an absorbent article having improved comfort, by the provision of breathability throughout the absorbent article which continues to maintain an acceptable level of protection.

It has now been found that this objective may be achieved by the provision of an article having a breathable backsheet which comprises at least one air permeable layer or apertured layer, such as an apertured formed film woven or nonwoven, which comprises and is preferably coated with a non soluble, liquid swellable material.

An advantage of the present invention is that the backsheet layer when in the dry state allows the transfer of moisture vapour and air and, in its wet state after swellage, the layer maintains at least a degree of moisture vapour permeability whilst preventing the transfer of liquids.

SUMMARY OF THE INVENTION

The present invention relates to absorbent articles such as diapers, sanitary napkins, panty liners incontinence products and the like. Typically such products comprise a liquid pervious topsheet, an absorbent core and a backsheet. The present invention is characterised in that the backsheet is a breathable backsheet and comprises at least one air permeable or apertured layer, said layer having an upper surface, a lower surface and an inner surface. According to the present invention at least one of the surfaces of the apertured backsheet layer has at least one region thereon, wherein said region of said surface comprises, and preferably is coated with, a non soluble, liquid swellable material. The present invention thus provides an absorbent article product which provides circulation of water vapour and air through the product when and where it is dry and preferably maintains water vapour permeability throughout the use of the product. Moreover, by the application of a swellable material onto the apertured backsheet layer, preferably as a coating, the present invention also provides absorbent articles having a reduced tendency to exhibit garment wet through.

DETAILED DESCRIPTION OF THE INVENTION

The absorbent article according to the present invention comprises as an essential component, a breathable backsheet. The backsheet typically extends across the whole of the absorbent structure and can extend into and form part of or all sideflaps, side wrapping elements or wings. The role of the backsheet is primarily to prevent the extrudes absorbed and contained in the absorbent structure from wetting articles that contact the absorbent product such as underpants, pants, pyjamas and undergarments thereby acting as a barrier to fluid transport. In addition however, the breathable backsheet of the present invention when dry permits the transfer of at least water vapour and preferably both water vapour and air through it and thus allows the circulation of gases into and out of the backsheet. In addition however the backsheet also preferably continues to allow the transfer of water vapour through it after wetting.

According to the present invention the breathable backsheet comprises at least one layer comprising apertures having a wearer facing surface hereinafter referred to as upper surface, a garment facing surface hereinafter referred to as lower surface and an inner surface. The term inner surface as used herein refers to any surface of said layer which is not the wearer facing or garment facing surface. Typically said inner surface, is a surface extending from the garment facing surface to the wearer facing surface thereby defining an aperture. Each of said wearer facing surface, said garment facing surface and said inner surface of said apertured backsheet layer has corresponding discrete regions thereon. The term region as utilised herein refers to a discrete surface area of said apertured layer which comprises an application of said non soluble liquid swellable material. Such regions are identified by discrete boundaries and may comprise a continuous or discontinuous application of said swelling material therein. According to the present invention at least one of said surfaces, preferably said wearer facing surface or said inner surface or a combination of said surfaces of said layer of said backsheet comprise said regions.

According to the present invention said regions of said surfaces typically comprise from 50% to 100% of the total surface area of each of said wearer facing, garment facing or inner surface respectively of said apertured backsheet layer. These regions may be located at any position of said surface. Typically, the wearer facing surface and the garment facing surface each have two end portions, two longitudinal side portions and one central portion and the region or regions are preferably located at least in the central portion of the surface. The term central portion as used herein is defined as the area of said surface where the largest liquid discharge occurs during article use. However, said region or regions may also be located in the end and longitudinal side portions of said surface. The number of regions present on said surface, will depend on the method of application used to apply the swellable material on to the surface and thus the surface may comprise one region or a plurality of regions. The regions may thus be regularly distributed in a pattern or irregularly distributed over one or each of the portions of said surface or over the complete one surface of the layer. Preferably, the regions repeat regularly over the entire surface, or the surface comprises one region extending over the entire surface.

Surprisingly, it has been found that the application of the swellable material onto said region of said surface of the apertured film layer or fibrous layer allows the material to swell to such an extent that once the layer is contacted with liquid, the liquid passage through the layer is substantially hindered. Whilst not being bound by theory it appears that the application of swellable materials to an apertured film or fibrous layer is advantageous because the apertures are distributed in a regular manner throughout the layers. In particular, it is believed that the regular dimensions, geometrical shape and distribution of the apertures throughout the layers allows the apertures to close more efficiently. As a result liquid penetration throughout the layer is prevented. In particular the present invention is especially beneficial in that the swellable material can be applied to the surface of the layer at the areas where maximum liquid discharge is known to occur and thus be effectively positioned so as to close the apertures on contact with the liquid. Furthermore, in embodiments wherein the inside surfaces of the apertured layer are coated, the closure of these apertures can be more effectively controlled.

According to the present invention any known material which swells when in contact with liquid is suitable for application to the surface or surfaces of the apertured backsheet layer. The term "swell" as used herein refers to a material exhibiting expansion when in contact with liquid in at least one direction i.e. in the x transverse direction, the y longitudinal direction or the z vertical direction or a material which swells in any combination of said directions.

The term liquid as used herein refers to any fluid containing at least 75% by weight of water, such as body fluids including urine, menstrual fluid and the like. The term non soluble as used herein refers to a material which is not significantly soluble at body temperature, such that it can be utilised for the desired function in absorbent articles.

According to the present invention each backsheet layer or layers comprising the swellable material swells in at least the x, y, or z direction. Typically, most suitable materials are isotropic and such that they swell in all 3 dimensions.

According to the test methods described hereafter said material preferably swells such that said apertured layer comprising said swellable material swells in the z direction of said apertured layer of the backsheet by at least 25%, preferably by at least 50%, more preferably at least 80%. However, swellage in the x and y directions is also desirable.

The incorporation of at least one apertured film layer comprising a swellable material in the breathable backsheet allows the passage of water vapour and preferably both water vapour and air through it. Thus, before use and whilst the backsheet remains dry, the absorbent article is at least permeable to water vapour. After contact with liquid, the material swells thereby tending to close the apertures of said layer of the backsheet. This thereby prevents the passage of macroscopic matter and liquids through the backsheet and onto the garments of the wearer. As a result of the swellage of the layer the air permeability of the layer and hence the backsheet overall is reduced and is typically negligible once the layer has become wet. However, an advantage of the present invention is that the passage of water vapour is not significantly hindered by the swelling action of the material on contact with liquids. Hence, whilst the air permeability is reduced the backsheet and consequently the absorbent article is still breathable even when wet.

According to the present invention any material exhibiting an ability to swell in contact with liquids is suitable for use herein. Suitable materials include (as non limitative examples) polymers such as polyvinyl alcohols having a hydrolysis level of at least 85%, preferably at least 95%, most preferably at least 98%. The polyvinyl alcohols are prepared by hydrolysis of polyvinyl acetate. The term hydrolysis level as used herein refers to the percent, in moles, of substitution of the acetate groups by hydroxyl groups.

Other suitable materials exhibiting an ability to swell in contact with liquids for use herein include (as non limitative examples) polymers such as crosslinked acrylic acid and its copolymers, especially in the form of full or partial salts of alkaline metals, alkaline-earth metals as well as aluminium, zinc and iron salts, as well as such as poly(methacrylic acid), polyacrylamide, poly(N,N-dimethylacrylamide), and polymethylacrylamide;

crosslinked poly-vinyl-pyrrolidone; copolymers of poly-vinyl-pyrrolidone particularly those containing vinyl acetate; polymethyl-, polyethyl- or polybutyl-vinyl ethers as well as the copolymers derived from vinyl ethers, for example, the copolymers of methyl-vinyl-ether and maleic anhydride or maleic acid;

polyethylene oxide having molecular weight from about 100,000 to 8,000,000 Daltons;

polysaccharides (gums) of natural origin and their semi-synthetic derivatives such as alginic acid and its salts, agar, locust bean gum, carrageenans, gelatin, starch and cellulose derivatives, such as carboxy-methyl-cellulose and cellulose acetate, pectin, guar gum and xanthan gum;

polyethylenimine; polyacrolein; styrene-maleic anhydride copolymers; ethylene-maleic anhydride copolymers; polydimethylaminoethyl methacrylate; polyalkylene polyamines; poly(vinylbenzyl-trimethylammonium chloride) as well as similar quaternary ammonium polymers; poly(maleic anhydride); lower molecular weight phenol-formaldehyde resins; lower molecular weight urea-formaldehyde resins as well as compatible blends of said swellable materials.

Preferred swellable materials for use herein are selected from polyvinyl alcohols; polyacrylic acid, its copolymers and derived salts; natural polysaccharides and their derivatives, as well as blends thereof. Furthermore, mixtures of swellable materials, which may exhibit different levels of swellability with liquid may also be utilized. In particular it has been observed that the swelling ability of particular combinations of certain swelling materials increases beyond the sum of the individual components. Such combinations of swelling materials which exhibit such synergy are particularly preferred and include for example the combination of polyacrylic acid and natural polysaccharide derivatives such as locust bean gum.

Any methods known in the art for the application of a material to a film or to a fibrous layer may be used to apply the swellable material to said apertured layer. Suitable methods include coating, spraying and dusting. Preferred methods are transfer coating for liquid swellable materials and dusting for particulate swellable materials. The swellable material may be applied to said region of said surface in any physical form including in the liquid form such as a melt, solution or emulsion, or in the solid form, such as particulates. Most preferably, the swellable material is applied to said apertured layer as a solid particulate such as granulate he particulate application is particularly preferred for utilization with apertured formed film layers.

The swellable material is preferably applied to the surface in an undiluted form. However, plasticising liquids (such as water, glycols, alcohols etc.) may also be utilised in order to apply the material to the region of the surface. Alternatively, binder materials such as carboxy methyl cellulose can also be used for applications when the swellable material is provided in particulate form.

Preferably the swellable material is applied to said surface in said region such that the resulting layer of particulates or coating of said swellable material has an average thickness of from 0.02 mm to 1 mm, preferably from 0.1 mm to 0.5 mm.

According to a preferred embodiment of the present invention the swellable material is applied to the regions of said surface, said layer in particulate form. Preferably, the particulates have an average diameter of from 0.01 to 1 mm, preferably from 0.03 mm to 0.5 mm prior to contact with liquid.

Independent of the manner in which the swellable material is applied to the surface or surfaces of the apertured layer, the material should preferably be applied at a basis weight of from 5 $g/m^2$ to 300 $g/m^2$, preferably from 10 $g/m^2$ to 250 $g/m^2$.

Dependent on the physical and chemical nature of the swellable material and the method utilised for its application, the swellable material may require the application of an adhesive in order to ensure its permanent attachment to the surface of the layer. However preferably, the swellable material does not require the presence of adhesive in order to ensure its retention. This may be achieved by the manner incorporation of the apertured layer into the backsheet construction and the absorbent article itself. Alternatively, the swellable material may have inherent adhesive properties itself such that additional adhesive is not required. Such materials include polyvinyl alcohols and polyvinyl methyl ether and other vinyl ethers. Similarly the apertured layer onto which the swellable material is applied may have adhesive properties such that an additional adhesive is not required.

In embodiments wherein an additional adhesive is required, any adhesives known in the art may be utilised and should be selected such as to minimise the effect of said adhesives on the ability of the material to swell and the ability of the apertured layer to allow the transfer of water vapour and air. Suitable adhesives for use in the present invention thus include waterborne acrylic adhesives for example Acronal V 205 available from BASF, Germany or EP 5560 F available from the Rohm and Haas Co. USA. It is also envisaged within the scope of the present invention to utilise adhesives which also have an inherent swelling capacity on contact with liquids, such they can contribute to the closure of the apertures of the layer on contact with water. Suitable adhesives include certain acrylic adhesives.

According to the present invention the adhesive may be applied to the swellable material prior to its application on the surface or the adhesive may be applied to the surface or surfaces directly before application of the swellable material. Accordingly the adhesive may be applied to said region utilising any method known in the art such as roll or bar coating, transfer, extrusion, spraying etc. Typically, the apertured layer is applied with from 2 g/m$^2$ to 30 g/m$^2$, preferably from 5 g/m$^2$ to 15 g/m$^2$ by weight of said layer of said adhesive.

Preferred breathable layers for use as backsheets herein are those having both a high moisture vapour and air exchange when dry and which preferably maintain a degree of moisture vapour permeability once wet, whilst preventing air exchange. According to a preferred embodiment of the present invention said apertured layer comprising the swellable material coating has an air permeability when dry of at least 50 l/(m$^2$ s), preferably at least 70 l/(m$^2$s) most preferably at least 100 l/(m$^2$s) and retains an air permeability, when wet, as described herein after under test methods, not higher than 30%, preferably less than 25% of the dry state air permeability value. Preferably, each apertured swellable layer has a air permeability when wet as described herein after under test methods of less than 10 l/(m$^2$s), and preferably less than 8 l/(m$^2$s).

According to the present invention suitable apertured layer comprising the swellable material can be selected from fibrous wovens, fibrous nonwovens, 2-dimensional microporous film, 2-Dimensional macroporous film, macroscopically expanded films or formed apertured films. Preferably, at least one, more preferably all of the swellable apertured layers of the backsheet are selected from 2-dimensional microporous, macroporous apertured film or a formed apertured film. Backsheets according to the present invention having more than one layer comprising a swellable material may therefore be selected from any of the above mentioned forms and may comprise any combination thereof According to the present invention the apertures of said layer of said backsheet may be of any configuration, but are preferably spherical or oblong. The apertures may also be of varying dimensions, but typically the apertures have an average diameter of from 5 micrometers to 600 micrometers. For example 2 dimensional planar porous films for use as said layer herein may have apertures having diameters from 200 micrometers to 5 micrometers. Similarly 2 dimensional planar microporous layers for use as said layer herein have apertures having average diameters of from 150 micrometers to 5 micrometers, preferably from 120 micrometers to 10 micrometers, most preferably from 90 micrometers to 15 micrometers. Suitable 2 dimensional planar macro porous layers have apertures having an average diameter of from 90 micrometers to 200 micrometers. Macroscopically expanded film layers and formed apertured layers have apertures having an average diameter of from 75 micrometers to 600 micrometers. The apertures preferably are evenly distributed across the entire surface of said layer. However, layers having only certain regions of the surface having apertures are also envisioned.

Suitable 2-Dimensional planar layers of the backsheet may be made of any material known in the art, but are preferably manufactured from commonly available polymeric materials. Suitable materials are for example XMP-1001 of Minnesota Mining and Manufacturing Company, St. Paul, Minn., USA and Exxaire XBF101W, supplied by the Exxon Chemical Company. As used herein the term 2-Dimensional planar layer refers to layers having a depth of less than 1 mm, preferably less than 0.5 mm, wherein the apertures have an average uniform diameter along their length and which do not protrude out of the plane of the layer. The apertured materials for use as a backsheet in the present invention may be produced using any of the methods known in the art such as described in EPO 293 482 and the references therein.

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured preformed films are uni directional such that they have at least substantially, if not complete one directional fluid transport towards the core.

Suitable macroscopically expanded films for use herein include films as described in for example in U.S. Pat. No. 4,637,819 and U.S. Pat. No. 4,591,523.

Preferably, said swellable material is applied to at least one of the surfaces of one of the backsheet layers. In multiple breathable backsheet embodiments wherein only one of the backsheet layers is applied with the swellable material of the present invention, the surface of the layer should be positioned towards the absorbent core, preferably such that said surface does not form the garment facing surface of the absorbent article. Most preferably the layer itself is positioned such that it is in direct contact with the absorbent core and the garment facing surface thereof is applied with swellable material. This ensures that the swellable material contacts the fluid as soon as it has passed through the absorbent core and can immediately swell thereby preventing wet through. The additional backsheet layers may be positioned in contact with the wearer facing or garment facing surface of the apertured backsheet layer.

According to the present invention said backsheet comprises at least one apertured layer comprising said non soluble liquid swellable material. However in addition, said backsheet may comprise optional additional layers which do not comprise swellable materials as defined herein. According to the present invention, said backsheet preferably comprises at least two layers and most preferably said backsheet consists of three layers. The additional backsheet layers can be of any form such as polymeric woven, nonwoven or apertured films such as 2-Dimensional, planar micro and macro-porous films, macroscopically expanded films and formed polymeric apertured films as described herein above. Furthermore, said additional layers may be of any chemical nature, as described herein above and may be formed from synthetic or naturally derived sources or mixtures thereof.

According to a preferred embodiment of the present invention the backsheet comprises at least two layers, a first apertured layer comprising said swellable material and a second layer comprising a non swellable polymeric layer comprising a fibrous woven, a fibrous nonwoven, a 2-Dimensional apertured porous film or a formed apertured film, most preferably the second layer is a fibrous nonwoven layer.

According to an alternative embodiment of the present invention the backsheet consists of three layers, said apertured layer comprising said non soluble, liquid swellable material and a second and a third layer both comprising non swellable components, wherein the second layer and the third layers comprise a polymeric fibrous nonwoven.

According to a preferred embodiment of the present invention the breathable backsheet itself comprising said layer has in the dry state, the air permeability at the levels defined herein above for the apertured layers comprising the swellable material.

According to the present invention the absorbent articles further comprise a topsheet and absorbent core. The absorbent material or core can be a fluffy fibrous absorbent core, comprising hydrogel particles if desired, or laminated tissues with or without particulate materials including hydrogel particles. The absorbent core fibres can be any of those known in the art including cellulose fibres or polymeric fibres rendered absorbent or even non absorbent matrix fibres. Also tissues of sufficient basis weight and absorbency can be used in the absorbent core according to the present invention.

Another component which may be included in the absorbent articles of the present invention, in particular in the core are odour control actives. Suitable actives include zeolites, silica, chelants such as ethylene diamine tetraacetic acid, active carbon and clays. These components can be in corporated in any form, but preferably as discrete particles.

According to the present invention the topsheet may comprise a single layer or a multiplicity of layers. In a preferred embodiment the topsheet comprises a first layer which provides the user facing surface of the topsheet and a second layer between the first layer and the absorbent structure/core. The topsheet provides a layer through which the liquids to be absorbed penetrate to the absorbent material.

The topsheet as a whole and hence each layer individually needs to be compliant, soft feeling, and non-irritating to the wearer's skin. It also can have elastic characteristics allowing it to be stretched in one or two directions. Typically, the topsheet extends across the whole of the absorbent structure and can extend into and form part of or all of the preferred sideflaps, side wrapping elements or wings. According to the present invention the topsheet may be formed from any of the materials available for this purpose and known in the art, such as non woven fabrics, films or combinations of both. In a preferred embodiment of the present invention at least one of the layers of the topsheet comprises a hydrophobic, liquid permeable apertured polymeric film. Preferably, the upper layer is provided by a film material having apertures which are provided to facilitate liquid transport from the wearer facing surface towards the absorbent structure, as detailed for example in U.S. Pat. No. 3,929,135, U.S. Pat. No. 4,151,240, U.S. Pat. No. 4,319,868, U.S. Pat. No. 4,324,426, U.S. Pat. No. 4,343,314 and U.S. Pat. No. 4,591,523.

According to the present invention the absorbent article is constructed by joining the various elements such as topsheet, backsheet and absorbent core by any means well known in the art. For example the backsheet and/or topsheet may be joined to the absorbent core or to each other by a uniform continuous layer of adhesive, a patterned layer of adhesive, or an array of separate lines, spirals or spots of adhesive. Alternatively, the elements may be joined by heat bonds, pressure bonds, ultra sonic bonds, dynamic mechanical bonds or any other suitable joining means known in the art and any combination thereof. Preferably the individual layers of the breathable backsheet are joined to each other so as to minimise and preferably eliminate any reduction in the vapour permeability of the backsheet Similarly, the breathable backsheet itself is joined to other elements of the absorbent articles so as to minimise the effect of the moisture vapour permeability of the backsheet.

According to the present invention the absorbent article may find utility as sanitary napkins, panty liners, adult incontinence products and baby diapers, but my also include other articles such as underarm pads or collar bands. The present invention finds particular susceptibility as sanitary napkins and panty liners. Thus, in addition to the components described herein above, the absorbent article may also comprise all those features and parts which are typical for products in the context of their intended use such as wings and side flaps, undergarment adhesive means, release paper, wrapping elements, fastening means and the like, all known in the art.

EXAMPLES

TEST METHODS

Air Permeability Test on Individual Swellable Layers of a Breathable Backsheet.

The air permeability test is utilised to assess the ability of a material to circulation/exchange of air.

Basic Principle of the Method.

The basic principle of the test is to evaluate the resistance of a material to the passage of air. This test measures the volume (or amount) of air that flows through a sample of given dimensions under standard conditions (of 23° C./50% relative humidity) and under a given difference of pressure. The instrument utilised for the test is: Air Permeabilimeter FX 3300 manufactured by TexTest AG Switzerland.

100 mm square of wet and dry samples were prepared as described below for air permeability measurements. The sample is placed on the device as instructed by the manufacturer. An aspiration pump is used to generate a depression of 1210 Pa that sucks air through the sample layer. The device measures the volume of air flow at constant pressure drop across the orifices that contains the sample and measurement head. Finally the device generates a value of air permeability in the units of "$1/(m^2s)$". For each material, in the dry and in the wet state, six samples are measured and the average value of air permeability is calculated.

Dry and Wet Samples

The term dry as used herein refers to a sample material stored at 23° C. and 50% relative humidity for at least 12 hours. The test is also carried out under these conditions.

The term wet as used herein refers to a sample material which has been uniformly contacted with 10 cm$^3$ of distilled water at 37° C. with a pipette. The excess water is removed by gently pressing the samples on blotting paper. The sample is left to stand for at least 60 seconds before the test is carried out, the test being carried out within 10 minutes after contacting with water.

Swellage Test

The ability of the material to swell was measured by determining the caliper of a test sample of a backsheet in the dry and wet state. This determines the swellage in the z direction.

A square sample of 100 mm size of the layer to be tested, is prepared for caliper (thickness) measurement in the dry and wet state. The samples calipers are measured by using a thickness measuring device App. 51D20, Type 02101, supplied by Lorentzen & Wettre, Sweden and following the instruction of the supplier. The thickness measuring device records the caliper of the sample pressed between the two measuring plates, when the exerted pressure reaches 20 g/cm$^2$. The average of three caliper readings of each sample is taken. Five samples for each material are tested and the value is the average value of these readings.

Backsheet Layer Examples

Example 1

This example is a backsheet comprised of two layers, a first layer and a second layer both comprising a polyester Nonwoven, having a basis weight of 40 g/m$^2$, (available from Suominen, Finland, under the codename F 4100/40). The wearer facing surface of the second layer is coated with a water based acrylic adhesive, (available from Rohm and Haas Co., USA under the codename EP 5560 F, at a basis weight of 10 g/m$^2$). Powder of an acrylic superabsorbent, basis weight 50 g/m$^2$ (available from Hoechst A. G. , Germany under the code name Sanwet 3746-1) is then dusted onto the whole wearer facing surface. The garment facing surface of the first layer is then placed on the wearer facing surface of the second layer. The first and second layers are held together in position by the utilisation of staples about the circumference of the layers.

Air Permeability in the dry state=4000 litres/(m$^2$·s)

Air permeability in the wet state=4 litres/(m$^2$·s)

Dry caliper=850 μm

Wet caliper=2390 μm

% Delta swellage in z direction=181%

From the above values, it can be observed that the exemplified backsheet layer has a negligible air permeability after contact with liquid and demonstrate a high degree of swelling such that the caliper of the wet samples is 181% greater than the caliper of the corresponding dry samples, even after a liquid contact time with water of 60 seconds.

Example 2

The example is identical to example 1 except that the swellable material is replaced by Locust Bean Gum powder (available from Franco Vanni Italy, under the trade name Albagum at a basis weight of 43 g/m$^2$). The Locust Bean Gum powder is bonded to the wearer facing surface of the first layer by the application of a water based acrylic adhesive, (available under the code name EP 5560 F, from Rohm and Haas Co., at a basis weight of 6 g/m$^2$.)

Air Permeability in the dry state=7350 litres/(m$^2$·s)

Air permeability in the wet state=4 litres/(m$^2$·s)

Dry caliper=825 μm

Wet caliper=1140 μm

% Delta swellage in z direction=38%

Example 3

This example is identical to example 2 except that the second layer has been replaced by an apertured formed film, (available from Tredegar Co., USA, under the code was S-225 MD 25, having a basis weight of 25 g/m$^2$). The wearer facing surface of the second layer was coated with an adhesive layer of a water based acrylic adhesive, (Available under the codename EP 5560 F, from Rohm and Haas Co. USA, at a basis weight of 10 g/m$^2$), and the Locust Bean Gum powder (available from Franco Vanni Italy under the name Albagum) is applied at a basis weight of 14 g/m$^2$.

The discontinuous coating of water swellable material was applied on the wearer facing surface of the apertured formed film, i.e. on the surface from which the cones protrudes.

Air Permeability in the dry state 645 litres/(m$^2$·s).

Air permeability in the wet state 24 litres/(m$^2$·s)

Dry caliper=800 μm

Wet caliper=1050 μm

% Delta swellage in z direction 31%

Example 4

This example is identical to example 3 except that the swellable material has been replaced by a powder of an acrylic superabsorbent (Sanwet 3746-1, available from Hoechst A. G., Germany at a basis weight of 25 g/m$^2$).

Air Permeability in the dry state=1090 litres 1 (m$^2$·s).

Air permeability in the wet state=134 litres/(m$^2$·s).

Dry caliper=845 μm

Wet caliper=1600 μm

% Delta swellage in z direction=89%

Examples 1 & 2, in which the swellable materials are kept positioned between nonwovens, allow to measure the actual overall swellage of the material in the z direction (because these materials are expected to be substantially isotropic it is reasonable that the same swellage happens in x, y and z direction). It should be noted that for Examples 3 and 4, the change in caliper is not a direct measure of the ability of the swellable material to swell. This is because some of the swellage actually occurs on the inside surface of the apertured formed film and is hence not directly detectable as an increase in caliper. Consequently, the percentage change in swellage is not as large as anticipated.

Example 5

In this example the backsheet comprises three layers, a first layer, second layer and a third layer, the second layer being intermediate the first and third layers. The first and third layer comprise a polyester Nonwoven, having a basis weight of 40 g/m$^2$, (available from Suominen, Finland, under the code F 4100/40). The second layer is a formed apertured film (available from Tredegar, under the code S-225 MD 25, having a basis weight of 25 g/m$^2$) wherein the cones protrude from the plane of the garment facing surface of the film. The garment facing surface of the first layer and the wearer facing surface of the third layer are coated with a water based acrylic adhesive (Acronal V 205, available from BASF, Germany). The swellable material is a superabsorbent material (available from Shokubai, Japan, under the trade name Aqualic L-74) and is dusted over the wearer facing surface of the second layer, so that the average final weight of Aqualic L-74 present into a square meter of apertured film is 95 g. The three layers are then stapled together at the periphery.

Air Permeability in the dry state=510 litres/(m$^2$·s).

Air permeability in the wet state=7 litres/(m$^2$·s).

The swelling test was not carried out on this example. However, from the air permeability measurements it can be clearly concluded that the apertures have closed so as to minimize air permeability and hence swelling has occurred as required.

What is claimed is:

1. An absorbent article comprising a liquid pervious topsheet, a backsheet and an absorbent core, said core being positioned between said topsheet and said backsheet and wherein said backsheet is breathable and said backsheet comprises at least one layer comprising apertures, said layer having an upper surface, a lower surface and an inner surface and comprising at least one of said surfaces of said apertured layer has at least one region thereon, wherein said region of said surface is coated with a non soluble, liquid swellable material, wherein said region of said inner surface comprises said liquid swellable material.

2. An absorbent article comprising a liquid pervious topsheet, a backsheet and an absorbent core, said core being positioned between said topsheet and said backsheet and wherein said backsheet is breathable and said backsheet comprises at least one layer comprising apertures, said layer having an upper surface, a lower surface and an inner surface and comprising at least one of said surfaces of said apertured layer has at least one region thereon, wherein said region of said surface is coated with a non soluble, liquid swellable material, wherein said region of said inner surface comprises said liquid swellable material, and wherein said layer is an apertured formed film.

3. An absorbent article comprising a liquid pervious topsheet, a backsheet and an absorbent core, said core being positioned between said topsheet and said backsheet and wherein said backsheet is breathable and said backsheet comprises at least one layer comprising apertures, said layer having an upper surface, a lower surface and an inner surface and comprising at least one of said surfaces of said apertured layer has at least one region thereon, wherein said region of said surface is coated with a non soluble, liquid swellable material, wherein said region of said inner surface comprises said liquid swellable material, wherein said layer is an apertured formed film, and wherein said liquid swellable material is in the form of a particulate.

* * * * *